(12) United States Patent
Dombrowsky et al.

(10) Patent No.: US 10,660,981 B2
(45) Date of Patent: May 26, 2020

(54) SYSTEM AND APPARATUS THEREOF FOR DESTROYING PATHOGENS ASSOCIATED WITH FOOTWEAR

(71) Applicant: HARBOR INNOVATIONS, LLC, Oyster Bay, NY (US)

(72) Inventors: Rachel Dombrowsky, Hewlett, NY (US); Christopher Montalbano, Huntington, NY (US); Andrew Martin, Bayport, NY (US); Philip Beamer, Northport, NY (US)

(73) Assignee: HARBOR INNOVATIONS, LLC, Oyster Bay, NY (US)

( * ) Notice: Subject to any disclaimer, the term of this patent is extended or adjusted under 35 U.S.C. 154(b) by 0 days.

(21) Appl. No.: 16/515,149

(22) Filed: Jul. 18, 2019

(65) Prior Publication Data

US 2019/0336632 A1 Nov. 7, 2019

Related U.S. Application Data

(62) Division of application No. 15/626,615, filed on Jun. 19, 2017.

(Continued)

(51) Int. Cl.
*A61L 2/24* (2006.01)
*A61L 2/10* (2006.01)
(Continued)

(52) U.S. Cl.
CPC ............... *A61L 2/24* (2013.01); *A47L 11/405* (2013.01); *A47L 23/02* (2013.01); *A61L 2/0047* (2013.01);
(Continued)

(58) Field of Classification Search
CPC . A61L 2/10; A61L 2/24; A61L 2/0047; A61L 2202/14; A61L 2202/20; A47L 23/26
See application file for complete search history.

(56) References Cited

U.S. PATENT DOCUMENTS 6,886,210 B2   5/2005  Dean
7,575,869 B2   8/2009  Wyrick et al.
(Continued)

FOREIGN PATENT DOCUMENTS

EP   1223989 A1   7/2002

OTHER PUBLICATIONS

International Search Report and Written Opinion corresponding to International Application No. PCT/US2014/065766 dated Feb. 26, 2015.

(Continued)

*Primary Examiner* — Wyatt A Stoffa
(74) *Attorney, Agent, or Firm* — Carter, DeLuca & Farrell LLP; George Likourezos, Esq.

(57) ABSTRACT

An apparatus for destroying pathogens includes a platform and an LED matrix panel. The platform has a portion configured to permit passage of ultraviolet light therethrough. The LED matrix panel is disposed below the portion of the platform and includes a grid and a plurality of discreetly-controlled, ultraviolet light LEDs (UV LEDs). The grid defines a plurality of cells. Each UV LED is associated with one cell such that the cells direct the ultraviolet light emitted by the UV LEDs upwardly through the portion of the platform to sanitize an object supported on the portion of the platform.

4 Claims, 9 Drawing Sheets

Related U.S. Application Data

(60) Provisional application No. 62/430,070, filed on Dec. 5, 2016.

(51) Int. Cl.
*A47L 23/02* (2006.01)
*E04F 15/024* (2006.01)
*A47L 11/40* (2006.01)
*A61L 2/00* (2006.01)

(52) U.S. Cl.
CPC .......... *A61L 2/10* (2013.01); *E04F 15/02405* (2013.01); *A61L 2202/14* (2013.01); *A61L 2202/15* (2013.01)

(56) References Cited

U.S. PATENT DOCUMENTS

| | | | |
|---|---|---|---|
| 7,875,869 B1* | 1/2011 | Shadan | A61L 2/0047 250/365 |
| 8,186,004 B2 | 5/2012 | Garcia et al. | |
| 8,203,124 B2 | 6/2012 | Havens et al. | |
| 8,277,741 B2* | 10/2012 | McCabe | A61L 2/10 422/186.3 |
| 8,378,324 B2 | 2/2013 | Gardner, III | |
| 8,466,433 B2 | 6/2013 | Ullman | |
| 8,470,239 B1 | 6/2013 | Kerr | |
| 8,617,479 B2 | 12/2013 | Gil et al. | |
| 8,624,202 B2 | 1/2014 | Gil | |
| 8,631,533 B1 | 1/2014 | Gulian et al. | |
| 8,721,119 B2 | 5/2014 | Chu et al. | |
| 8,784,731 B2 | 7/2014 | Gil et al. | |
| 9,135,838 B2 | 9/2015 | Kline et al. | |
| 9,198,991 B2* | 12/2015 | Dombrowsky | A61L 2/10 |
| 9,211,352 B2 | 12/2015 | Kassel et al. | |
| 9,579,410 B2 | 2/2017 | Simmons et al. | |
| 9,764,050 B1* | 9/2017 | Almeida | A61L 2/10 |
| 9,801,965 B2 | 10/2017 | Bettles et al. | |
| 9,848,727 B2 | 12/2017 | Day et al. | |
| 2008/0310996 A1 | 12/2008 | Kim et al. | |
| 2009/0004047 A1 | 1/2009 | Hunter et al. | |
| 2009/0314308 A1 | 12/2009 | Kim et al. | |
| 2010/0104470 A1* | 4/2010 | McCabe | H05B 47/105 422/22 |
| 2010/0193709 A1 | 8/2010 | Dalton | |
| 2011/0041452 A1* | 2/2011 | Uhlig | A47G 27/0431 52/716.8 |
| 2011/0240883 A1* | 10/2011 | Ullman | A61L 2/10 250/454.11 |
| 2012/0167325 A1 | 7/2012 | Omidi | |
| 2012/0187313 A1 | 7/2012 | Clark et al. | |
| 2013/0101461 A1 | 4/2013 | Gil et al. | |
| 2013/0154441 A1 | 6/2013 | Redmond | |
| 2013/0177474 A1 | 7/2013 | Kerr | |
| 2013/0259742 A1 | 10/2013 | Kerr | |
| 2014/0170019 A1* | 6/2014 | Gil | A01N 1/0294 422/24 |
| 2015/0106710 A1* | 4/2015 | Dirschus | G06F 3/04847 715/708 |
| 2015/0132183 A1 | 5/2015 | Dombrowsky et al. | |
| 2015/0196674 A1* | 7/2015 | Newham | A61L 2/10 250/455.11 |
| 2015/0217011 A1 | 8/2015 | Bettles et al. | |
| 2015/0306267 A1* | 10/2015 | Selker | A61L 2/0035 340/10.42 |
| 2015/0308091 A1 | 10/2015 | Foust et al. | |
| 2015/0335246 A1* | 11/2015 | Rains, Jr. | F21V 23/003 362/231 |
| 2015/0335775 A1* | 11/2015 | Toso | A61L 2/18 422/29 |
| 2016/0175896 A1* | 6/2016 | Montgomery | B08B 7/0057 250/454.11 |
| 2016/0324997 A1 | 11/2016 | Dayton | |
| 2017/0035918 A1* | 2/2017 | Kassel | A61L 2/10 |
| 2017/0165385 A1 | 6/2017 | Eliason et al. | |
| 2019/0142981 A1* | 5/2019 | Kim | G01B 5/24 250/455.11 |
| 2019/0240363 A1* | 8/2019 | Kreiner | A61L 2/0047 |

OTHER PUBLICATIONS

Sensacell, Interactive panel-lighting system, www.sensacell.com, 15 pages (Sep. 2015), retrieved from Internet Archive, https://web.archive.org/web/20150926105310/http://www.sensacell.com/wp-content/uploads/2013/09/Sensacell-Application-Doc-1.1.pdf, 1 page (Feb. 2019).

International Preliminary Report on Patentability dated Jun. 11, 2019 including a Written Opinion of the International Searching Authority dated Jan. 4, 2018 corresponding to counterpart Int'l Application PCT/US2017/058439.

"Ultraviolet" Wikipedia, Apr. 2, 2019. (Year: 2019).

European Search Report dated Dec. 12, 2019 corresponding to counterpart Patent Application EP 17878875.8.

* cited by examiner

SYSTEM AND APPARATUS THEREOF FOR DESTROYING PATHOGENS ASSOCIATED WITH FOOTWEAR

CROSS-REFERENCE TO RELATED APPLICATION

The present application claims priority to, and the benefit of, U.S. patent application Ser. No. 15/626,615 filed on Jun. 19, 2017, which claims priority to U.S. Provisional Application Ser. No. 62/430,070 which was filed Dec. 5, 2016, the entire contents of both applications are incorporated by reference herein.

BACKGROUND

1. Technical Field

The present disclosure relates to devices for cleaning footwear. More specifically, the present disclosure relates to an apparatus that uses ultraviolet light to destroy or inhibit the growth of surface pathogens, such as, for example, virus, bacteria, mold, spore, and fungi, and/or to reduce chemical contaminants.

2. Background of Related Art

The soles of people's footwear are a primary vehicle for pathogens entering homes and healthcare facilities. The pathogens can cause sickness, disease, and possible death. Door mats, the primary means for cleaning shoe bottoms, remove dirt but not pathogens, and can quickly become an incubator for germs. Other solutions such as liquid dips are not practical for high traffic areas and require frequent maintenance to stay effective. Disposable booties or shoe covers are used in professional environments, but do not work well in public areas, as people tend to be self-conscience about wearing them, and there are safety concerns over people tripping while wearing such covers.

Other technologies used to sanitize footwear include devices that incorporate light bulbs that emit short-wavelength ultraviolet ("UV-C") light directed at the bottom of footwear to destroy pathogens that may be associated therewith. These devices, however, are typically bulky due to the large size of the UV-C light bulbs, they may be ineffective at preventing or limiting unintended exposure to the UV-C light, and are oftentimes difficult to operate.

SUMMARY

In one aspect of the present disclosure, an apparatus for destroying pathogens is provided. The apparatus includes a platform and an LED matrix panel. The platform has a portion configured to permit passage of ultraviolet light therethrough. The LED matrix panel is disposed below the portion of the platform and includes a grid defining a plurality of cells, and a plurality of discreetly-controlled, ultraviolet light LEDs (UV LEDs) that selectively emit ultraviolet light. Each UV LED is associated with one of the cells such that the cells direct the ultraviolet light emitted by the UV LEDs upwardly through the portion of the platform to sanitize an object supported on the portion of the platform.

In some embodiments, the apparatus may further include a plurality of visible light emitting LEDs (V LEDs) each electrically linked to a corresponding UV LED. Each V LED may be disposed adjacent its corresponding UV LED and may be configured to emit visible light concurrently with the emission of ultraviolet light from the corresponding UV LED.

In some embodiments, the apparatus may further include a processor in communication with the UV LEDs and the V LEDS. The processor may be configured to selectively activate the V LEDs to emit a first color of visible light upon the corresponding UV LED being in an ON state, and a second color of visible light upon the corresponding UV LED being in an OFF state.

In some embodiments, the UV LEDs may be further configured as photodiodes such that the UV LEDs sense a change in light upon an object being disposed on the portion of the platform to activate the UV LEDs.

In some embodiments, the apparatus may further include a pressure sensor coupled to the platform and in communication with the UV LEDs. The UV LEDs may be configured to be activated upon the pressure sensor sensing a threshold force.

In some embodiments, the apparatus may further include a plurality of sensors. The sensors may be disposed within a respective one of the cells. A first UV LED may be activated in response to a first sensor sensing an object on the portion of the platform. The first UV LED and the first sensor may be disposed within the same cell. The first sensor may sense the object only when the object is disposed directly above the first sensor.

In some embodiments, the sensors may be infrared sensors and/or photodiodes.

In some embodiments, the grid may include a plurality of spaced apart longitudinal walls and a plurality of spaced apart transverse walls in a crisscrossing arrangement with the longitudinal walls. The longitudinal and transverse walls may together define the cells.

In some embodiments, the platform may include a frame and a pair of plates. The frame may define a pair of openings and may be fabricated from a material that prevents the transmission of ultraviolet light. The plates may be fabricated from quartz and may be disposed within a respective opening. The quartz permits the transmission of ultraviolet light therethrough.

In some embodiments, each of the plates may define an outer periphery that is in abutment with a respective inner side wall of the frame. The outer periphery of each of the plates may be sealed to the respective inner side walls of the frame.

In some embodiments, the apparatus may further include a housing assembly in which the LED matrix panel is disposed. The LED matrix panel may be thermally coupled to an inner surface of the housing assembly.

In some embodiments, the LED matrix panel may include a printed circuit board on which the UV LEDS are situated. The printed circuit board may be thermally coupled to a bottom housing of the housing assembly.

In another aspect of the present disclosure, a footwear-sanitizing system is provided and includes a user interface to be mounted to a wall, and an apparatus to be disposed on a floor. The user interface is configured to display a progress of a sanitization process. The apparatus is in communication with the user interface and includes a platform and an LED matrix panel. The platform has a portion configured to permit passage of ultraviolet light therethrough. The LED matrix panel is disposed below the portion of the platform and includes a grid and a plurality of discreetly-controlled, ultraviolet light LEDs (UV LEDs) that selectively emit ultraviolet light. The grid defines a plurality of cells and each UV LED is associated with one of the cells such that the cells direct the ultraviolet light emitted by the UV LEDs upwardly through the portion of the platform to sanitize an object supported on the portion of the platform.

In some embodiments, the system may further include a processor in communication with each of the UV LEDs, the V LEDS, and the user interface. The processor may be configured to selectively activate the V LEDs of the apparatus and lights of the user interface to emit a first color of visible light upon the corresponding UV LED being in an ON state, and a second color of visible light upon the corresponding UV LED being in an OFF state.

In yet another aspect of the present disclosure, a method of installing a footwear-sanitizing system is provided and includes mounting a user interface to a wall of a room, positioning the apparatus on a floor of the room, and connecting the user interface and the UV LEDS of the apparatus to an external power source.

Further details, advantages, and aspects of exemplary embodiments of the present disclosure are described in more detail below with reference to the appended figures.

As used herein, the terms parallel and perpendicular are understood to include relative configurations that are substantially parallel and substantially perpendicular up to about + or −10 degrees from true parallel and true perpendicular.

BRIEF DESCRIPTION OF THE DRAWINGS

Embodiments of the present disclosure are described herein with reference to the accompanying drawings, wherein.

DETAILED DESCRIPTION

Figure 1:
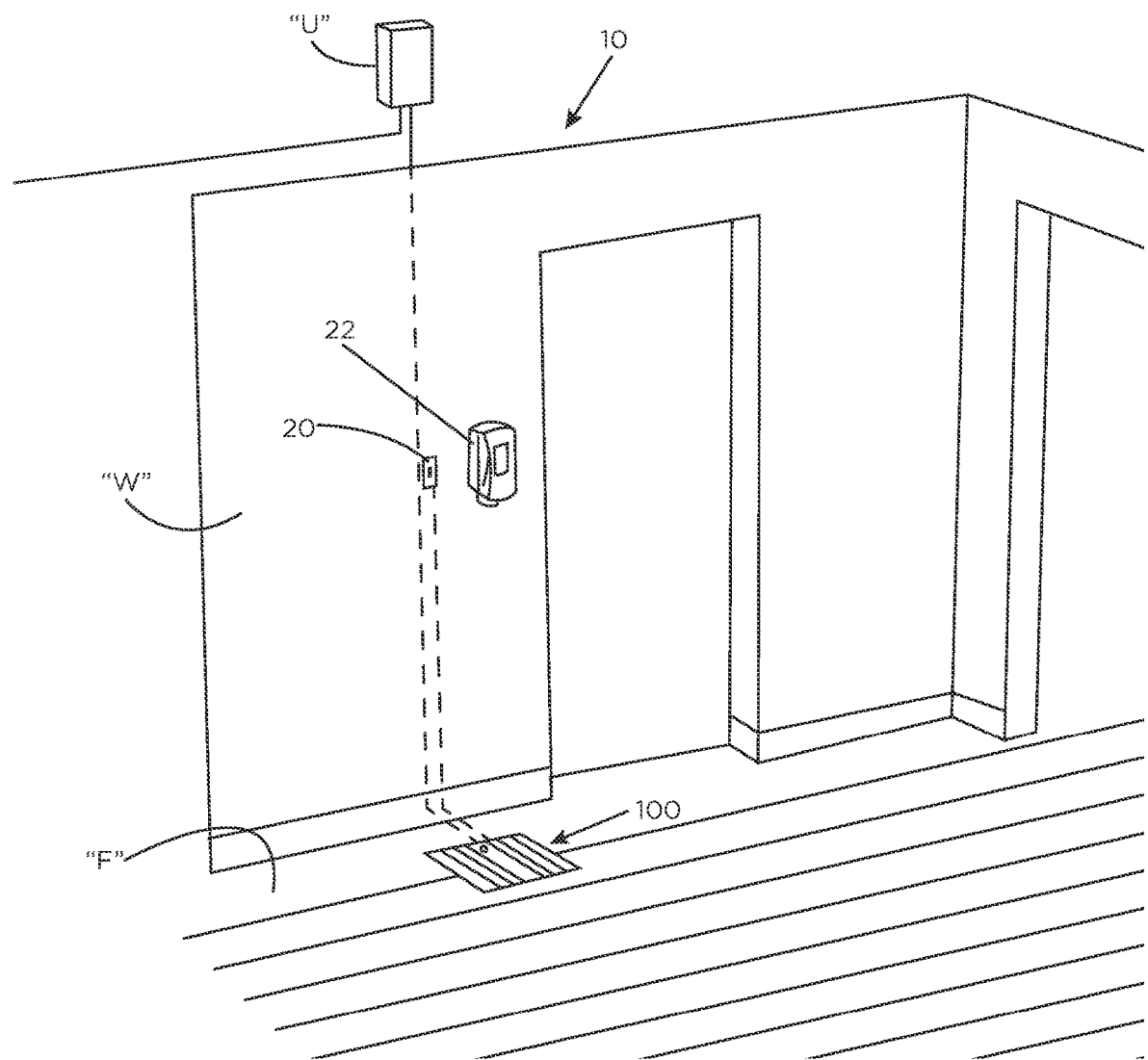
FIG. 1 is a perspective view a footwear-sanitizing system including a footwear sanitizer and a user interface each installed in an operating room in accordance with the principles of the present disclosure.

Embodiments of the presently disclosed system and apparatus for destroying pathogens are described in detail with reference to the drawings, in which like reference numerals designate identical or corresponding elements in each of the several views.

As used herein, the term "pathogen" includes, but is not limited to, viruses, bacteria (e.g., *Staphylococcus aureus*, MRSA, CDIF, VRE, *Pseudomonas aeruginosa* and *E. coli*), molds, spores, fungi, or the like.

The present disclosure provides a footwear-sanitizing system that utilizes UV-C light-emitting LEDs to sanitize footwear in a variety of settings including, but not limited to, hospitals, homes, laboratories, etc. The UV-C LEDs are smaller than standard UV-C light bulbs allowing for a miniaturization of the overall footwear-sanitizing system. The UV LEDs are disposed on a printed circuit board and within individual cells of a grid. Each of the UV LEDs are discreetly controlled such that only those UV LEDs disposed directly below the feet of a user will be activated. Due to the UV LEDs being disposed within cells of the grid, the ultraviolet light is directed upwardly through a platform and onto the bottom of the footwear of the user to destroy pathogens associated therewith. These and further details of the footwear-sanitizing system will be described below.

With reference to FIGS. 1-7, a sanitizing system, such as a footwear-sanitizing system 10 is illustrated and generally includes an apparatus or footwear sanitizer 100 to be installed in or on a floor "F" of a room, a user interface 20 to be mounted on a vertically-extending wall "W" of the room, and a hand-sanitizing station 22. The user interface 20 and the apparatus 100 are in communication with one another and are each externally powered by an external power source via an electrical connection (e.g., wires or wireless connection). The apparatus 100 is structured to support the weight of a user and to destroy pathogens associated with footwear worn by the user.

With reference to FIGS. 2-5, the apparatus 100 includes a housing assembly 102 and an LED matrix panel 120 disposed within the housing assembly 102. The housing assembly 102 includes a top housing or platform 102a and a bottom housing 102b, which when coupled to one another cooperatively define an internal cavity for housing components of the apparatus 100. The housing assembly 102 may have a square shape, but in some embodiments may assume any suitable size and shape such as trapezoidal, circular, rectangular, triangular, or the like. The platform 102a of the housing assembly 102 includes a frame 104 and a pair of plates 106a, 106b supported by the frame 104. The frame 104 and the bottom housing 102b may be fabricated from a non-corrosive material that prevents the transmission of ultraviolet light therethrough. In some embodiments, the frame 104 and the bottom housing 102b may be fabricated from any suitable material, such as, for example, various metals, including aluminum.

The frame 104 of the platform 102a has a pair of openings 108a, 108b defined through a thickness thereof. The openings 108a, 108b are dimensioned to securely capture the respective plates 106a, 106b therein. In particular, the frame 104 of the platform 102a has a pair of inner side walls 110a, 110b, and a pair of ledges 112a, 112b extending perpendicularly from the inner side walls 110a, 110b and into the respective openings 108a, 108b. The plates 106a, 106b are disposed on the ledges 112a, 112b of the frame 104 such that a top surface of each of the plates 106a, 106b is flush with a top surface of the frame 104. An outer periphery 114a, 114b of each of the plates 106a, 106b is in abutting engagement with the respective inner side walls 110a, 110b of the frame 104 such that all four sides of the plates 106a, 106b are encased by the inner side walls 110a, 110b of the frame 104. A sealant "S" may be applied between the inner side walls 110a, 110b of the frame 104 and the outer periphery 114a, 114b of the plates 106a, 106b to form an air-tight seal therebetween.

The plates 106a, 106b of the platform 102a are elongated and sized to accommodate any size foot of a person standing on the platform 102a. The plates 106a, 106b have a rectangular shape, but it is contemplated that the plates 106a, 106b may assume any suitable shape dimensioned to accommodate an entire foot of a person. The plates 106a, 106b are received within the respective openings 108a, 108b of the frame 104 and are formed from a material (e.g., quartz) that permits the passage of UV-C light therethrough while also exhibiting sufficient strength to support the weight of a person. In some embodiments, the plates 106a, 106b may be fabricated from materials other than quartz, such as fused silica, glass, ruby, or the like.

With continued reference to FIGS. 2-5, the LED matrix panel 120 of the apparatus 100 is disposed below and in alignment with the openings 108a, 108b of the frame 104 of the platform 102a, and in turn, the plates 106a, 106b of the platform 102a. The LED matrix panel 120 includes a plurality of ultraviolet light LEDs ("UV LEDs") 122 and a grid 124. The UV LEDs 122 are discreetly controlled by a processor "P" in communication with a printed circuit board 126 of the LED matrix panel 120. The UV LEDs 122 emit short-wavelength ultraviolet radiation ("UV-C light"). In some embodiments, UV LEDs 122 may be configured to emit other wavelengths of ultraviolet light instead of or in addition to UV-C light. The UV LEDs 122 are arranged on the printed circuit board 126 in a series of longitudinally-extending rows, but in some embodiments the UV LEDs 122 may be arranged on the printed circuit board 126 in any suitable pattern, whether random or defined. The UV LEDs 122 are powered by a power source (not shown) disposed externally of the apparatus 100. In some embodiments, the UV LEDs 122 may be replaced with ultraviolet light-emitting bulbs.

The grid 124 of the LED matrix panel 120 is fabricated from a material that prevents transmission of ultraviolet light therethrough, such as, for example, a thermoplastic resin. In some embodiments, inner surfaces of the grid 124 may be coated with a reflective material that reflects ultraviolet light. The grid 124 includes a plurality of spaced apart longitudinal walls or bars 124a and a plurality of spaced apart transverse walls or bars 124b crisscrossing with the longitudinal walls 124a. The longitudinal and transverse walls 124a, 124b together define a plurality of discreet chambers or cells 128. The cells 128 are illustrated as having a square configuration, but it is contemplated that the cells 128 may have any suitable shape, such as, for example, circular, triangular, rectangular, oblong, uniform, non-uniform, or the like.

The grid 124 is supported on the printed circuit board 126 such that one UV LED 122 of the plurality of UV LEDs 122 is received in a respective one of the plurality of cells 128 of the grid 124. In this way, the UV LEDs 122 are partitioned off from adjacent UV LEDs 122 so that ultraviolet light emitted by one UV LED 122 is prevented from escaping laterally into adjacent cells 128 of the grid 124. Additionally, the longitudinal and transverse walls 124a, 124b of the grid 124 are perpendicular to a plane defined by the printed circuit board 126, whereby the ultraviolet light emitted from the UV LEDs 122 is directed or guided perpendicularly upward relative to the printed circuit board 126. This construction will prevent UV-C light scattering in directions other than directly upward.

The printed circuit board 126 of the LED matrix panel 120 may be directly or indirectly thermally coupled to an inner surface of the housing assembly 102. In particular, the printed circuit board 126 may be thermally coupled to an inner surface of the bottom housing 102b of the housing assembly 102. As such, heat generated by the LED matrix panel 120 during use may be directly transmitted from the printed circuit board 126 and into the thermally conductive housing assembly 102 to facilitate cooling of the LED matrix panel 120 and the overall internal environment of the apparatus 100.

The printed circuit board 126 of the LED matrix panel 120 is in communication with the processor "P," which selectively activates particular UV LEDs 122 based on where on the platform 102a a user's foot is positioned, as will be described. The processer "P" may be operably connected to a memory, which may include transitory type memory (e.g., RAM) and/or non-transitory type memory (e.g., flash media, disk media, etc.), collectively referred to as "memory" herein. The memory may store instructions (e.g., software), which when executed on the processor "P" causes one or more footwear sanitizing sequence(s) to be performed by the apparatus 100. More particularly, when the instructions are executed on the processor "P," the processor "P" transmits control signals to one or more of the described components in electrical communication, either wired or wireless, with the processor "P." The processor "P" may additionally receive sensor signals from the one or more components in communication with the processor "P." Those skilled in the art will appreciate that the processor "P" may be substituted by using any logic processor (e.g., control circuit) adapted to perform the calculations and/or set of instructions described herein including, but not limited to, field programmable gate arrays, digital signal processor, and combinations thereof.

Figure 3:
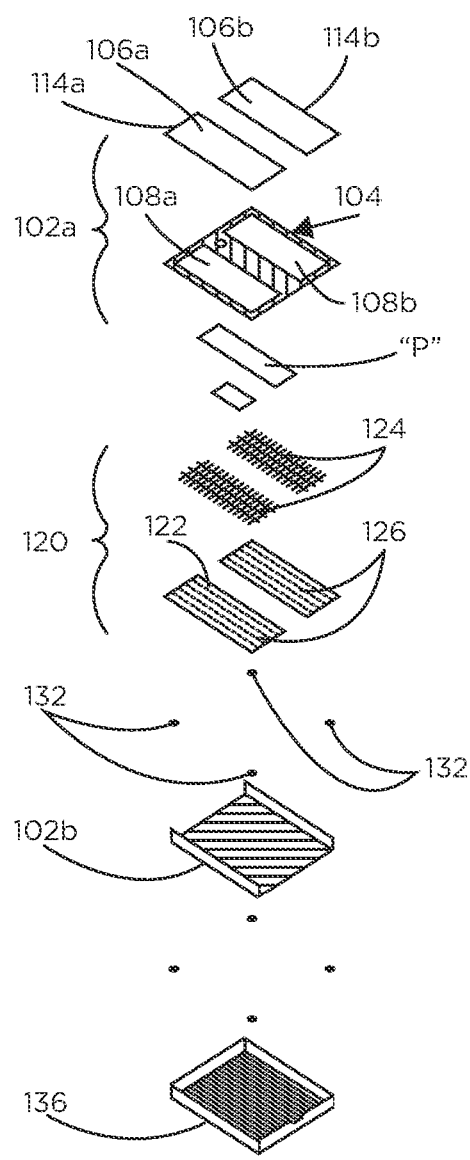
FIG. 3 is a perspective view, with parts separated, of the footwear sanitizer of FIG. 2.
Figure 4:
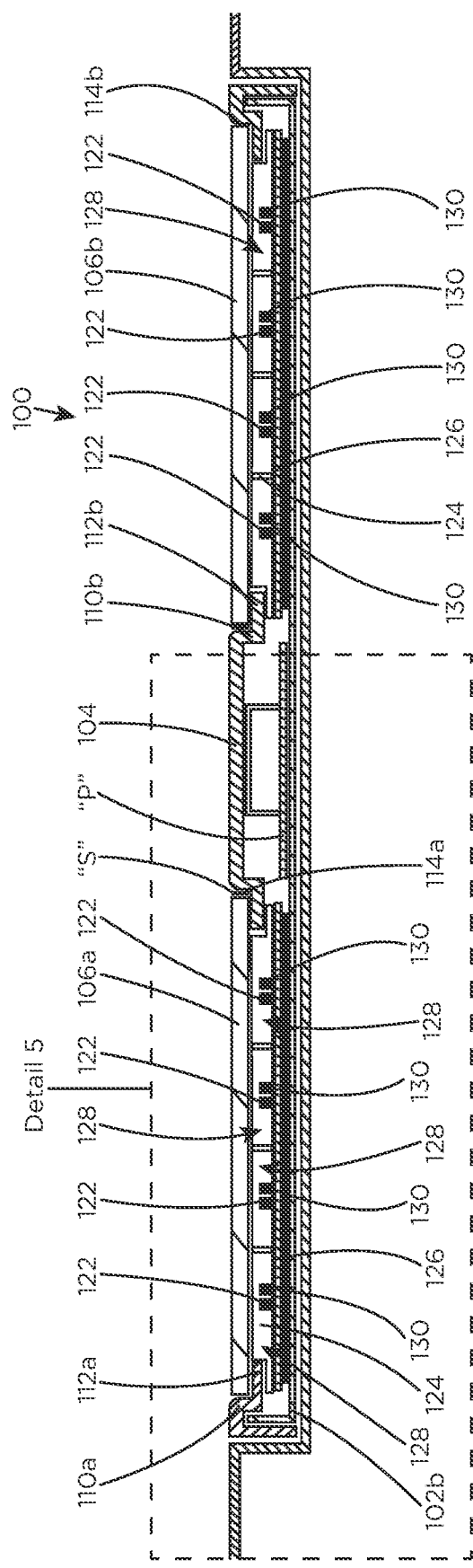
FIG. 4 is a cross-section, taken along line 4-4 of FIG. 2, of the footwear sanitizer.
Figure 5:
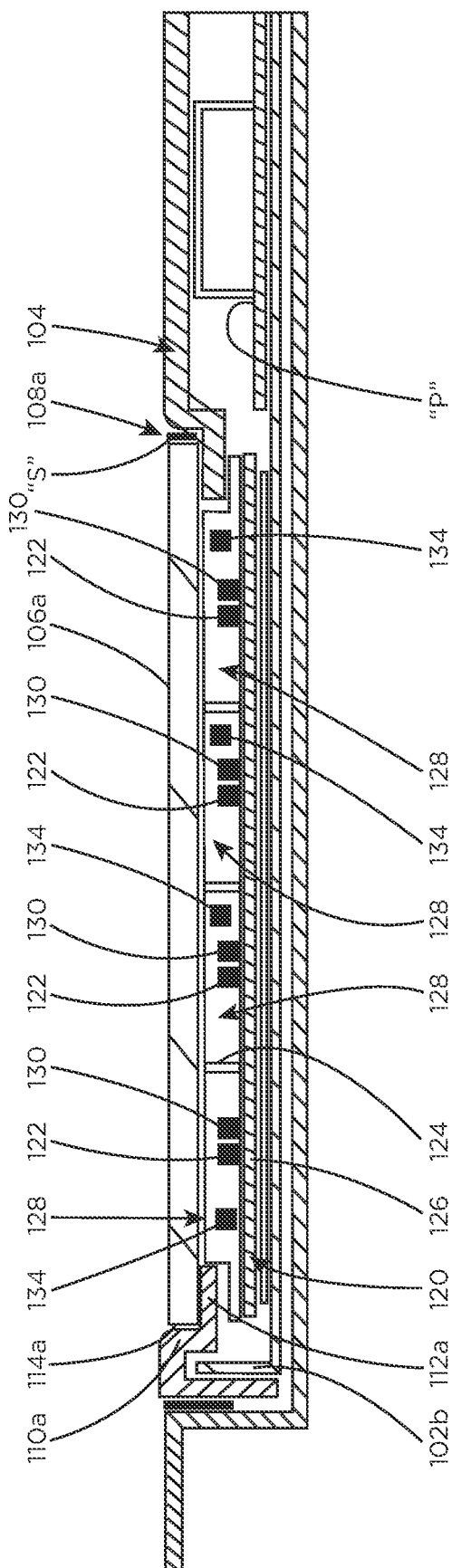
FIG. 5 is an enlarged view of a portion of the footwear sanitizer indicated as detail 5 in FIG. 4.

With reference to FIGS. 3-5, the apparatus 100 may include a plurality of visible light emitting LEDs ("V LEDs") 130 arranged on the printed circuit board 126 of the LED matrix panel 120. Each of the V LEDs 130 may selectively emit a variety of colors of visible light (e.g., blue, green, purple, etc.). One V LED 130 of the plurality of UV LEDs 130 is received in a respective one of the plurality of cells 128 of the grid 124, and each V LED 130 is disposed adjacent to and directly electrically linked with one corresponding UV LED 122. As such, a state of the UV LED 122 (e.g., ON or OFF) and a state of the respective V LED 130 (e.g., ON, OFF, or a type of color illuminated) will be synchronized, as will be described in further detail below.

Since UV-C light is not visible to the human eye, a user of the apparatus 100 will be unable to determine whether the UV LEDs 122 are turned on based solely on the appearance of the UV LEDs 122. Thus, the V LEDs 130 may act as status indicators for the UV LEDs 122 by switching on and off concurrently with the UV LEDs 122. More specifically, the processor "P" may be in communication with the UV LEDs 122 and the V LEDs 130 and may be programmed to selectively activate the V LEDs 130 to emit a particular color(s) based on the status of the associated UV LED 122. For example, when a set of UV LEDs 122 are in an OFF state, the processor "P" may direct the V LEDs 130 associated with the set of UV LEDs 122 to emit a first color (e.g., green) indicating to a user that the UV LEDs 122 are in the OFF state. Similarly, when the set of UV LEDs 122 are in an ON state, the processor "P" may direct the V LEDs 130 associated with the set of UV LEDs 122 to emit a second color (e.g., purple) indicating to the user that the UV LEDs 122 are in the ON state. It is contemplated that because the V LEDs 130 are directly electrically linked with the respective UV LEDs 122, the processor "P" will not be required to activate the V LEDs 130.

With continued reference to FIGS. 3-5, the apparatus 100 may include a pressure sensor or sensors 132 for determining when a user is standing on the platform 102a of the apparatus 100. The pressure sensors 132 may be disposed between the frame 104 of the housing assembly 102 and the bottom housing 102b of the housing assembly 102. The pressure sensors 132 are in communication with the UV LEDs 122 and/or the processor "P." The processor "P" may be configured to activate (i.e., switch on) the UV LEDs 122 in response to the pressure sensors 132 sensing a threshold force greater than approximately 40 to 70 lbs. As such, the UV LEDs 122 will remain in the OFF or inactive state until the pressure sensors 132 sense a user standing on the platform 102a. In some embodiments, each cell 128 of the LED matrix panel 120 may include a pressure sensor 132, each of which being electrically coupled to the corresponding UV LED 122 and V LED 130.

In addition to or in the alternative of having pressure sensors 132, the apparatus 100 may include light sensors 134, such as, for example, infrared sensors or photodiodes. One light sensor 134 may be disposed in each cell 128 of the grid 124 and may be electrically coupled to the UV LED 122 and V LED 130 disposed within that cell 128. Due to the light sensors 134 being disposed directly below the plates 106a, 106b of the platform 102a, the light sensors 134 sense a presence or absence of an object (e.g., footwear) on the plates 106a, 106b of the platform 102a. The light sensors 134 may be configured to sense the presence or absence of an object on the plates 106a, 106b of the platform 102a via sensing a change in infrared heat, a change in visible light, or a change in any other detectable form of electromagnetic radiation.

The light sensors 134 are also in communication with the processor "P" and are configured to signal to the processor "P" when they detect an object on the plates 106a, 106b of the platform 102a. The processor "P" is configured to activate only the UV LEDs 122 that are disposed in the cells 128 of the light sensors 134 that detect the object. Accordingly, only the set of UV LEDs 122 disposed directly beneath the object will be activated by the processor "P," whereas the UV LEDs 122 disposed outside of the boundary of the object remain in an OFF state.

In some embodiments, instead of the apparatus 100 having distinct light sensors, the UV LEDs 122 may assume the dual function of being a UV light emitting diode and a light sensing photodiode that senses a change in light upon an object being disposed on the plates 106a, 106b of the platform 102a.

Figure 6:
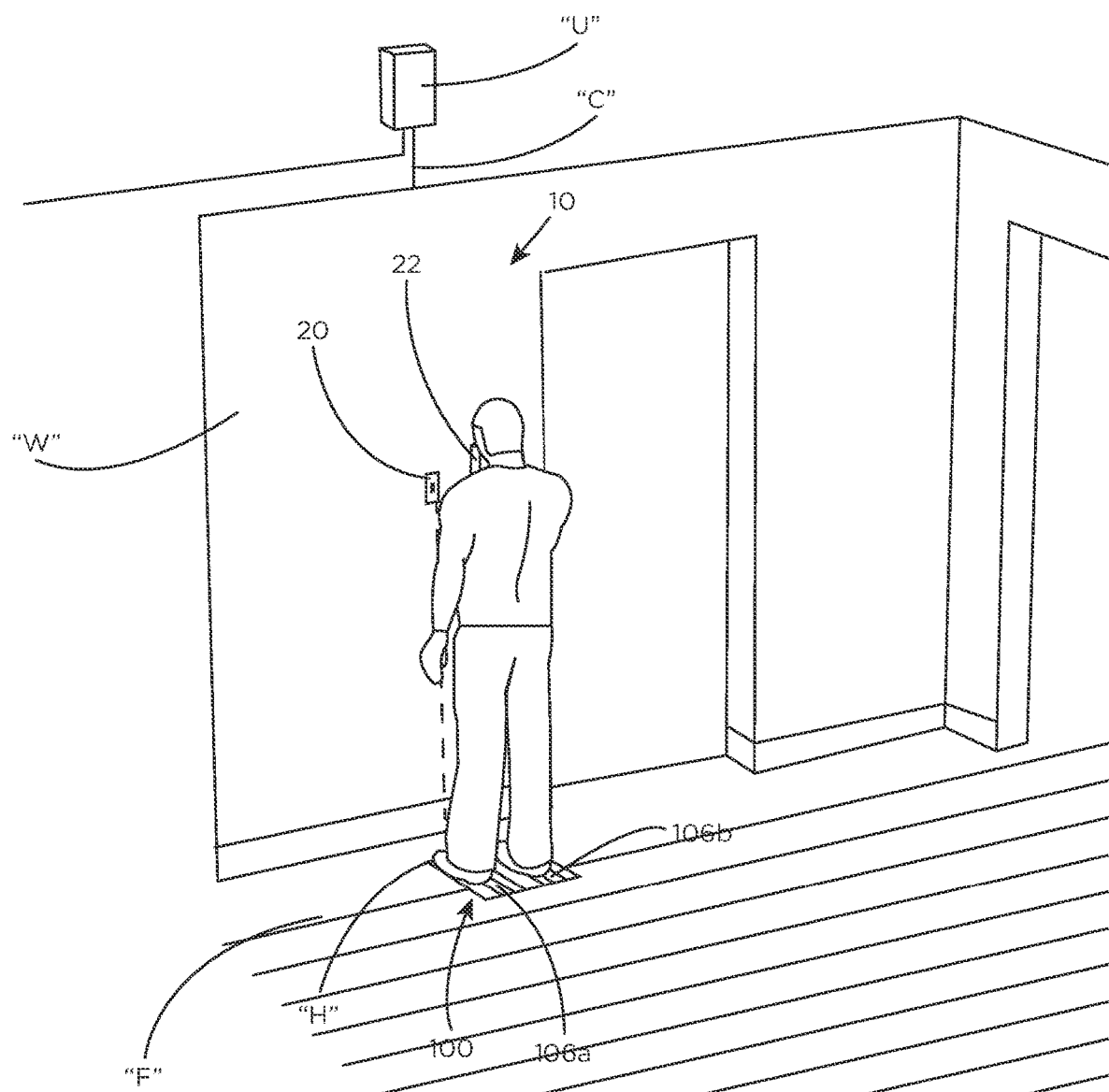
FIG. 6 is a perspective view of the footwear-sanitizing system of FIG. 1, illustrating a person standing on the footwear sanitizer and interacting with the user interface.

In operation, with reference to FIG. 6, a user desiring to sanitize their footwear may position their feet on the pair of plates 106a, 106b of the apparatus 100. Prior to standing on the plates 106a, 106b, the V LEDs 130 may emit a green color to invite the user to stand on the apparatus 100. By initially standing on the apparatus 100, the pressure sensors 132 sense the weight of the user and signals to the processor "P" that the apparatus 100 is ready for use, thereby switching the apparatus 100 from an inactive mode to an active mode. It is envisioned that if the pressure sensors 132 do not sense the threshold amount of weight, the apparatus 100 will remain in the inactive mode. The UV LEDs 122 may be automatically activated by the processor "P" upon the pressure sensors 132 sensing the threshold weight. Alternately, the user may press a button on the user interface 20 to initiate the sanitizing process.

The light sensors 134, which are disposed directly beneath the feet of the user, will detect a change in light, e.g., from the infrared emitted by the feet of the user or a decrease in the amount of visible light reaching the light sensors 134 due to the user's feet blocking light from reaching the light sensors 134. Upon the light sensors 134 detecting the change in light, the processor "P" activates only those UV LEDs 122 disposed in the same cells 128 of the grid 124 as the light sensors 134 that detected the change in light. Concurrently with the activation of the selected UV LEDs 122, the V LEDs 130 associated with the activated LEDs 122 are also activated to emit another color (e.g., purple) to indicate to the user that the UV LEDs 122 are turned ON. It is contemplated that all of the V LEDs 130 may be activated rather than only the V LEDs 130 associated with the activated UV LEDs 122. The user interface 20 may also be configured to emit the same color as the V LEDs 130 so that the user can be aware of the status of the apparatus 100 without having to look down.

As the activated UV LEDs 122 emit UV-C light, the walls 124a, 124b of the grid 124 direct the UV-C light upwardly at a perpendicular angle relative to the printed circuit board 126. The UV-C light passes uninterrupted through the pair of plates 106a, 106b of the platform 102a and contacts the bottom surfaces of the user's footwear to sanitize the footwear. The UV LEDs 122 remain activated for a preset amount of time predetermined to sufficiently destroy all pathogens. Upon the UV LEDs 122 being deactivated, the user interface 20 and the V LEDs 130 emit a color (e.g., green) indicating that the sanitizing process is complete and that the user may step off from the apparatus 100. The user interface 20 may also display an indication to the user that the sanitizing sequence is complete. For example, the user interface 20 may display a thumbs-up symbol when the sequence is completed. It is also contemplated that the user interface 20 may display a countdown to completion during the sanitizing sequence.

In embodiments, the processor "P" may receive and store information regarding each use of the sanitizing system 10. For example, the processor "P" may store the number of uses of the apparatus 100, the time of each use, whether each use was complete, identification information pertaining to the person using the apparatus 100, etc. This information may be utilized to assist in enforcing compliance with hospital or laboratory rules. It is also contemplated that clinicians who use the apparatus 100 may be equipped with an RFID tag storing at least their name and identification number, and/or the clinicians may be required to input their identification information prior to using the apparatus 100.

Figure 7:
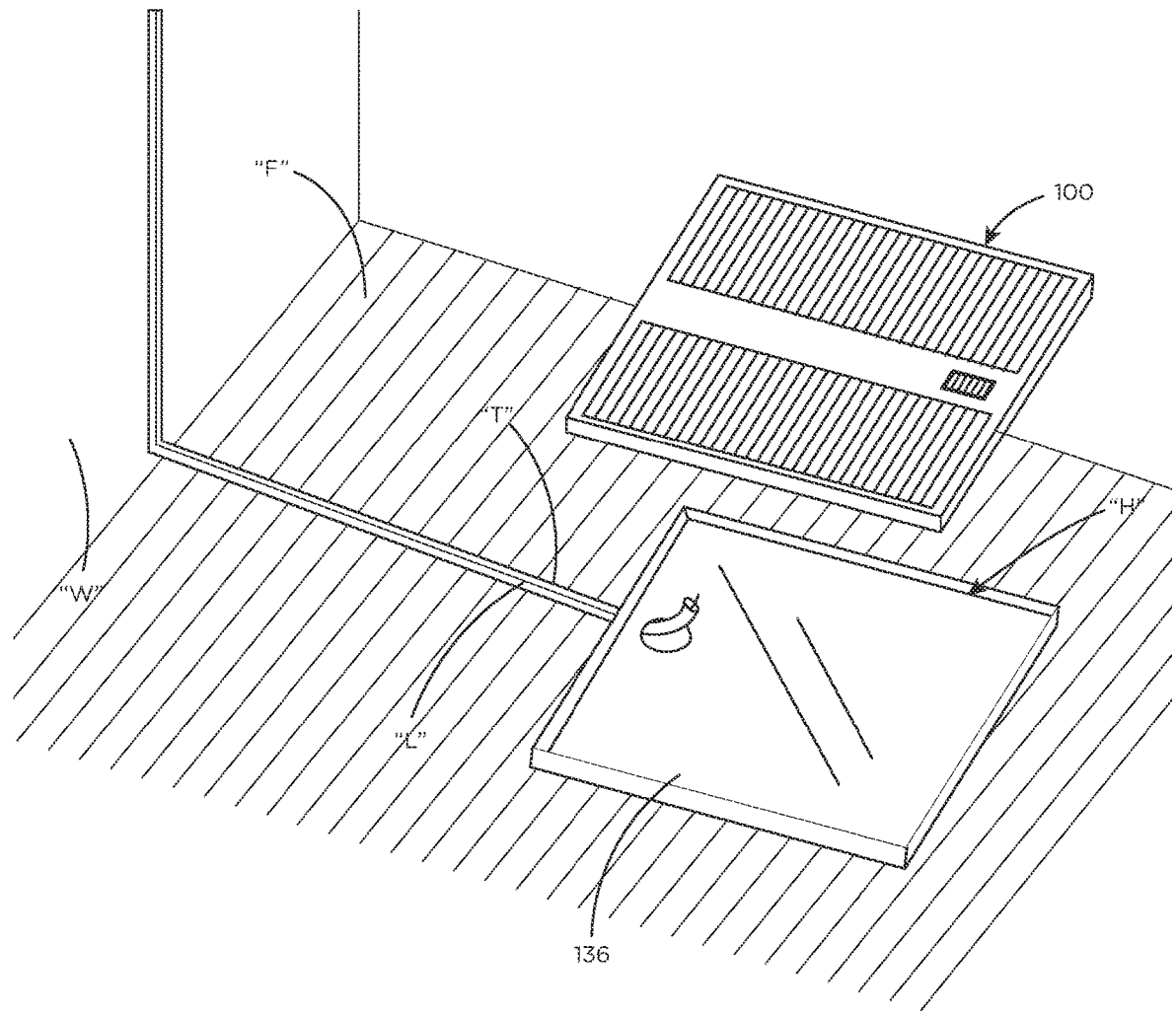
FIG. 7 is a perspective view of the footwear-sanitizing system of FIG. 1, illustrating the footwear sanitizer thereof installed into a floor of the operating room.

With reference to FIGS. 6 and 7, to install the footwear-sanitizing system 10, a hole "H" may be formed in the flooring "F" of a room to accommodate the apparatus 100 therein. A trench "T" may also be formed in the flooring "F" that leads from a wall "W" of the room into the hole "H." In embodiments, due to the apparatus 100 being thinner than other footwear sanitizing apparatus, the apparatus 100 may be placed directly on the floor rather than in a hole in the floor and "mud-up" to the apparatus 100 with a cement ramp and then tile over it. An install pan 136 may be deposited into the hole "H" prior to positioning the apparatus 100 into the hole "H." The apparatus 100 is connected to an external power source (not explicitly shown) via a utility box "U" (FIG. 1) mounted to the wall "W." Due to the apparatus 100 being powered by the utility box "U," the apparatus 100 does not have an internal power source, allowing the apparatus 100 to be manufactured with a much smaller footprint than if it required an internal power source. The user interface 20 is mounted to the wall "W" and coupled to a power line "L" that runs through the trench "T." By dropping the apparatus 100 into the hole "H," a top surface of the apparatus 100 is flush with a top surface of the flooring "F." In embodiments, a building may be provided that includes a plurality of the sanitizing systems 10 installed in various rooms of the building.

Figure 8:
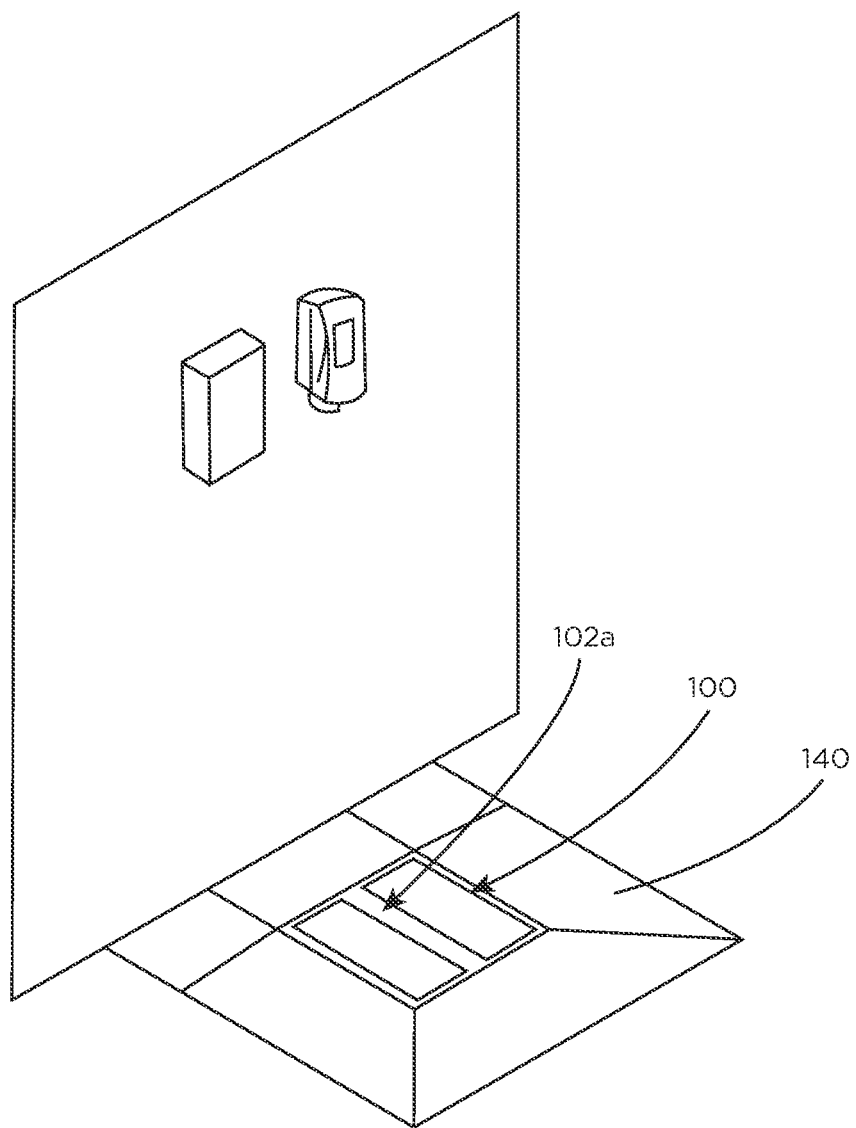
FIG. 8 is a perspective view of another embodiment of a footwear-sanitizing system including a footwear sanitizer and a user interface each installed in an operating room in accordance with the principles of the present disclosure.

In another embodiment, as shown in FIG. 8, instead of dropping the apparatus 100 into a hole in the floor, the apparatus 100 may sit on top of the floor and have a ramped outer shell 140 surrounding the apparatus 100 that transitions from the floor to the platform 102a of the apparatus 100.

Figure 9:
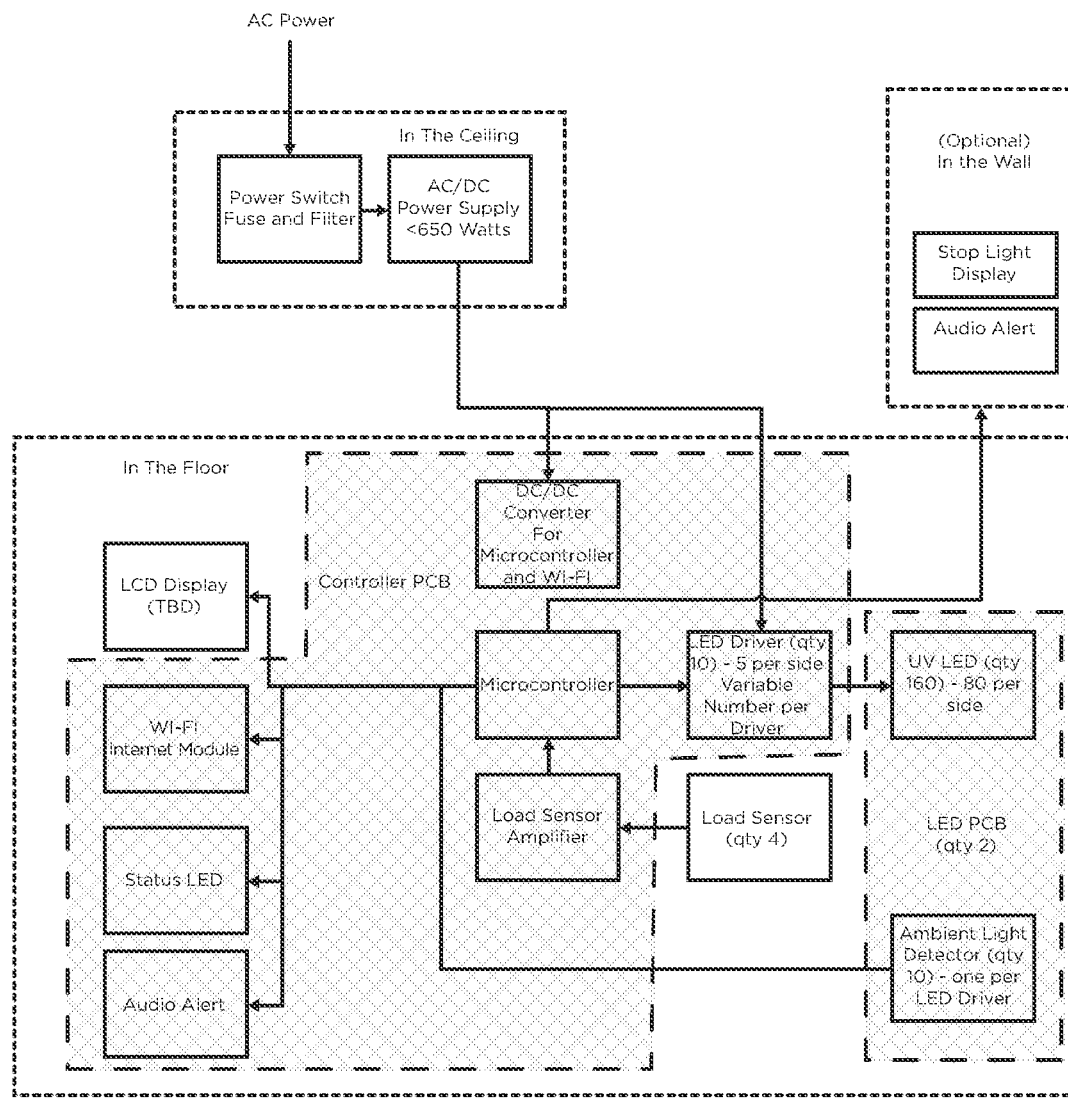
FIG. 9 is a block diagram illustrating the sanitizing system of FIG. 1 installed in a room.

With reference to FIG. 9, illustrated is a block diagram of the sanitizing system 10 including the apparatus 100, an external power converter 142, and an optional user interface 20. The power converter 142 receives electrical energy from an external power supply (not shown) which may be in the form of alternating or direct current. The electrical energy is received by a power switch 144 of the power converter 142. When the sanitization system 10 is activated or otherwise in use, the power switch 144 transfers the electrical energy to a power supply 146 of the power converter 142. The power supply 146 converts the electrical energy, if received in the form of alternating current (AC), into direct current (DC) to be transmitted to the internal components of the apparatus 100, including a microcontroller converter 156 and an LED driver 158. In response to receiving power from the power supply 146, the microcontroller converter 156 and the led driver 158 transmit the electrical energy to the microcontroller 154, and the UV LEDs 122, respectively.

The microcontroller 154 of the apparatus 100 includes the processor "P" and memory (not shown), the microcontroller 154 being in electrical communication with the LED driver 158, the ambient light detector or sensor 134, an audio device 150, the V LEDs 130, and a wireless communication module 148. The microcontroller 154 is also configured to transmit control signals to, and receive sensor signals from, the LED driver 158, an LCD display 121, a wireless communication module 148, an audio device 150, and the ambient light detector 134. The microcontroller 154 is further configured to transmit power to the V LEDs 130 to cause the V LEDs 130 to transmit light. The microcontroller 154, microcontroller converter 156, wireless communication module 148, V LEDs 130, audio device 150, load sensor amplifier 152, and LED driver 158 are disposed on and connected by circuits located along a printed circuit board or controller board 160.

It is contemplated that the wireless communication module 148 may be any suitable wireless communication device configured to transmit and receive sensor signals such as, without limitation, radio frequency, optical, Wi-Fi®, Bluetooth®, ZigBee®, or the like.

The audio device 150 may include any suitable speaker for transmitting audio signals to one or more users. The audio signals are determined by the microcontroller 154 in response to operation of the sterilization system 10, the control signals being transmitted to the audio device 150 upon generation. In response to receiving control signals from the microcontroller 154, the audio device transmits audio signals at one or more frequencies.

The load sensor amplifier 152 receives sensor signals from the pressure or load sensor 132 based on the application of a downward force to the apparatus 100 by a user or object, the sensor signals corresponding to a load measurement taken while the user or object is located on the apparatus 100. Based on the sensor signals received from the load sensor 132, the load sensor amplifier 152 transmits sensor signals to the microcontroller 154. The microcontroller 154 may subsequently generate control signals based on the sensor signals received by the load sensor amplifier 152 during operation of the sterilization system 10. For example, when a user is standing on the apparatus 100, once a predetermined load has been reached (e.g., 40-70 lbs of downward force applied to the top surface of the apparatus 100), the microcontroller 154 may transmit control signals to cause one or more of the UV LEDs 122 to transmit UV-C light. Additionally, or alternatively, when a user or object is standing or located on the apparatus 100, if the predetermined load has not been reached, the microcontroller 154 may not generate control signals to cause the one or more UV LEDs 122 to transmit UV-C light. It is contemplated that the microcontroller 154 may transmit control signals which cause the UV LEDs 122 to transmit UV-C light at varying intensities depending on the sensed load.

Figure 2:
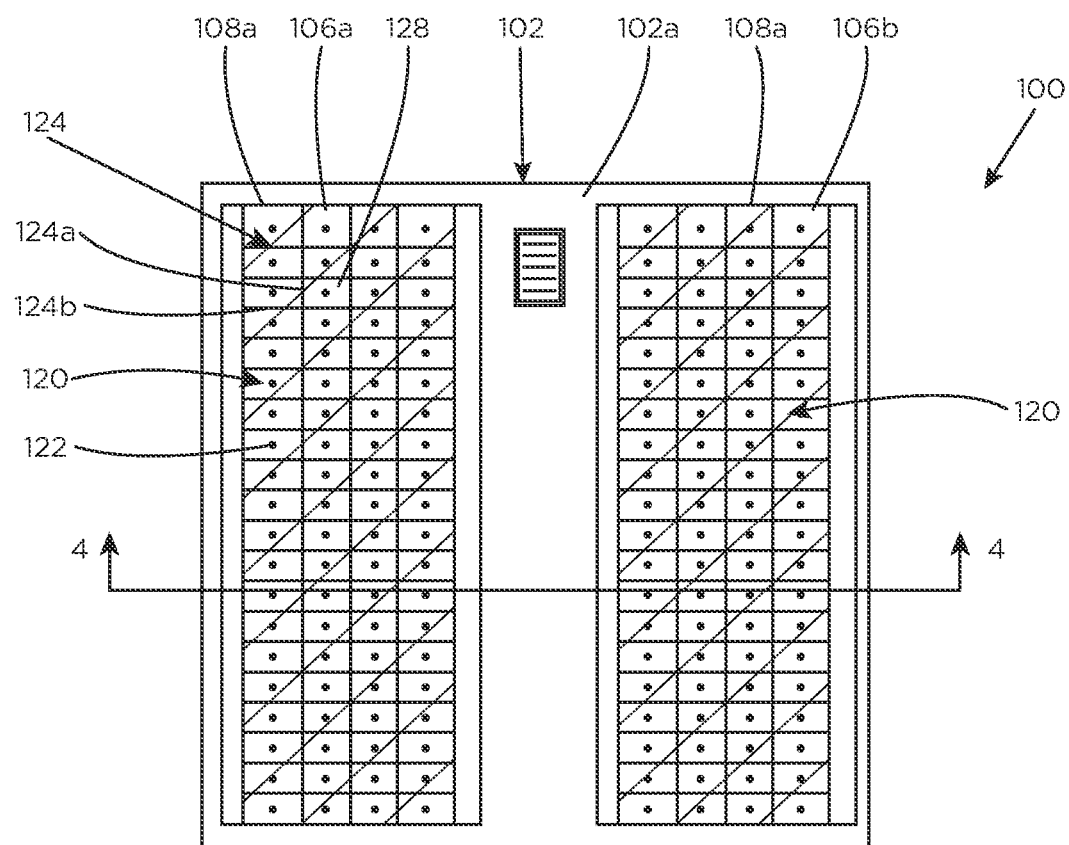
FIG. 2 is a top view of the footwear sanitizer of FIG. 1.

The LED driver 158 receives control signals from the microcontroller 154 as well as electrical power from the power supply 146. Based on the control signals received from the microcontroller 154, the LED driver 158 transmits electrical power to one or more of the UV LEDs 122 to cause the UV LEDs 122 to transmit UV-C light to the plates 106a, 106b (FIG. 2). It is contemplated that the UV-C light may be transmitted at varying or constant intensity levels.

The microcontroller 154 is configured to transmit control signals and/or electrical energy to the user interface 20 to control a stop light display 162 and/or an audio output device 164 of the user interface 20. More particularly, the microcontroller 154 may transmit control signals to the stop light display 162 similar to signals transmitted to the V LEDs 130 to cause both the stop light display 162 and V LEDs 130 to project light corresponding to operation of the sanitization system 10. Additionally, the microcontroller 154 may transmit control signals to the audio output device 164 to transmit audio signals in response to operation of the sterilization system 10.

It will be understood that various modifications may be made to the embodiments disclosed herein. Therefore, the above description should not be construed as limiting, but merely as exemplifications of various embodiments. Those skilled in the art will envision other modifications within the scope and spirit of the claims appended thereto.

The invention claimed is:

1. An apparatus for destroying pathogens, comprising:
a platform having a portion configured to permit passage of ultraviolet light therethrough; and
an LED matrix panel disposed at least partially below the portion of the platform and including:
 a grid defining a plurality of cells;
 a plurality of discreetly-controlled, ultraviolet light LEDs (UV LEDs) that selectively emit ultraviolet light, wherein each UV LED of the plurality of UV LEDs is associated with one cell of the plurality of cells such that the plurality of cells direct the ultraviolet light emitted by the plurality of UV LEDs upwardly through the portion of the platform to sanitize an object supported on the portion of the platform;
 a plurality of visible light emitting LEDs (V LEDs) each electrically linked to a corresponding UV LED of the plurality of UV LED; and
a processor in communication with the plurality of UV LEDs and the plurality of V LEDS and configured to selectively activate the V LEDs to emit:
a first color of visible light upon the corresponding UV LED being in an ON state; and
a second color of visible light upon the corresponding UV LED being in an OFF state.

2. The apparatus according to claim 1, wherein each V LED of the plurality of V LEDs is disposed adjacent the corresponding UV LED and is configured to emit visible light concurrently with the emission of ultraviolet light from the corresponding UV LED.

3. A footwear-sanitizing system, comprising:
a user interface to be mounted to a wall, the user interface configured to display a progress of a sanitization process; and
an apparatus to be disposed on a floor, the apparatus in communication with the user interface and including:
a platform having a portion configured to permit passage of ultraviolet light therethrough; and
an LED matrix panel disposed below the portion of the platform and including:
a grid defining a plurality of cells;
a plurality of discretely-controlled, ultraviolet light LEDs (UV LEDs) that selectively emit ultraviolet light, wherein each UV LED of the plurality of UV LEDs is associated with one cell of the plurality of cells such that the plurality of cells direct the ultraviolet light emitted by the plurality of UV LEDs upwardly through the portion of the platform to sanitize an object supported on the portion of the platform; and
a plurality of visible light emitting LEDs (V LEDs) each electrically linked to a corresponding UV LED of the plurality of UV LEDs, wherein each V LED of the plurality of V LEDs is disposed adjacent the corresponding UV LED and is configured to emit visible light concurrently with the emission of ultraviolet light from the corresponding UV LED; and
a processor in communication with each of the plurality of UV LEDs, the plurality of V LEDS, and the user interface, the processor being configured to selectively activate the V LEDs of the apparatus and lights of the user interface to emit:
a first color of visible light upon the corresponding UV LED being in an ON state; and
a second color of visible light upon the corresponding UV LED being in an OFF state.

4. A method of installing a footwear-sanitizing system, comprising:
mounting a user interface to a wall of a room;
providing an apparatus for destroying pathogens, the apparatus including:
a platform having a portion configured to permit passage of ultraviolet light therethrough; and
an LED matrix panel disposed below the portion of the platform and including:
a grid defining a plurality of cells; and
a plurality of discretely-controlled, ultraviolet light LEDs (UV LEDs) that selectively emit ultraviolet light, wherein each UV LED of the plurality of UV LEDs is associated with one cell of the plurality of cells such that the plurality of cells direct the ultraviolet light emitted by the plurality of UV LEDs upwardly through the portion of the platform to sanitize an object supported on the portion of the platform;
electrically linking a plurality of visible light emitting LEDs (V LEDs) each to a corresponding UV LED of the plurality of UV LEDs;
positioning the apparatus on a floor of the room;
connecting the user interface and the UV LEDS of the apparatus to an external power source;
disposing each V LED adjacent to the corresponding UV LED and configuring each V LED to emit visible light concurrently with the emission of ultraviolet light from the corresponding UV LED;
installing a processor in communication with each of the plurality of UV LEDs, the plurality of V LEDS, and the user interface; and
configuring the processor to selectively activate the V LEDs of the apparatus and lights of the user interface to emit:
a first color of visible light upon the corresponding UV LED being in an ON state; and
a second color of visible light upon the corresponding UV LED being in an OFF state.

* * * * *